US009669121B2

(12) United States Patent
Liao et al.

(10) Patent No.: US 9,669,121 B2
(45) Date of Patent: Jun. 6, 2017

(54) ULTRAVIOLET LIGHT SOURCE AND METHODS

(71) Applicant: RayVio Corporation, Hayward, CA (US)

(72) Inventors: Yitao Liao, Hayward, CA (US); Robert Walker, Hayward, CA (US); Doug Collins, Hayward, CA (US); Sheung Li, Hayward, CA (US)

(73) Assignee: RAYVIO CORPORATION, Hayward, CA (US)

( * ) Notice: Subject to any disclaimer, the term of this patent is extended or adjusted under 35 U.S.C. 154(b) by 0 days.

(21) Appl. No.: 14/745,315

(22) Filed: Jun. 19, 2015

(65) Prior Publication Data

US 2016/0093412 A1    Mar. 31, 2016

Related U.S. Application Data

(63) Continuation-in-part of application No. 14/704,888, filed on May 5, 2015, which is a continuation-in-part of application No. 14/645,290, filed on Mar. 11, 2015.

(30) Foreign Application Priority Data

Sep. 25, 2014    (CN) .......................... 2014 1 0499470

(51) Int. Cl.
*A61L 2/10*    (2006.01)
*G01N 21/64*    (2006.01)
*G01N 21/94*    (2006.01)

(52) U.S. Cl.
CPC ............ *A61L 2/10* (2013.01); *G01N 21/6456* (2013.01); *G01N 21/6486* (2013.01); *G01N 21/94* (2013.01); *G01N 2201/0221* (2013.01); *G01N 2201/062* (2013.01)

(58) Field of Classification Search
CPC ..................................... G21K 5/02; A61L 2/10
IPC ......................................................... G21K 5/02
See application file for complete search history.

(56) References Cited

U.S. PATENT DOCUMENTS

| | | | | |
|---|---|---|---|---|
| 8,884,258 B1 * | 11/2014 | Liao | .......................... | A61L 2/08 250/504 H |
| 2006/0275171 A1 * | 12/2006 | Younts | ...................... | A61L 2/02 422/24 |
| 2013/0063922 A1 * | 3/2013 | La Porte | ................... | A61L 2/10 361/807 |

(Continued)

*Primary Examiner* — David Porta
*Assistant Examiner* — Faye Boosalis
(74) *Attorney, Agent, or Firm* — Richard T. Ogawa; Ogawa P.C.

(57) ABSTRACT

A method for a hand-held device comprising illuminating, with a first UV LED associated with the hand-held device, a surface of an object with UV light, acquiring with a visible-light image sensor on the hand-held device, a first image of the surface of the object while the surface of the object is illuminated by the first UV LED, performing with the processor in the hand-held device, a function upon the first image to determine a type of contaminant disposed upon the surface of the object, determining with the processor in the hand-held device, sanitation techniques to perform in response to the type of contaminant that is determined, and displaying with a touch-screen display on the hand-held device, the sanitation techniques to the user.

20 Claims, 7 Drawing Sheets

(56) References Cited

U.S. PATENT DOCUMENTS

| | | | |
|---|---|---|---|
| 2014/0264070 A1* | 9/2014 | Bettles | A61L 2/10 250/430 |
| 2015/0070319 A1* | 3/2015 | Pryor | G06F 3/0425 345/175 |
| 2015/0090904 A1* | 4/2015 | Cole | A61L 2/10 250/492.1 |
| 2015/0209457 A1* | 7/2015 | Bonutti | A61L 2/10 250/435 |
| 2015/0209459 A1* | 7/2015 | Kreitenberg | A61L 2/10 250/492.1 |
| 2016/0000951 A1* | 1/2016 | Kreiner | A61L 2/0047 422/24 |

* cited by examiner

ULTRAVIOLET LIGHT SOURCE AND METHODS

CROSS-REFERENCE TO RELATED APPLICATIONS

The present invention is a continuation-in-part of U.S. patent application Ser. No. 14/704,888 filed May 5, 2015, that is a continuation-in-part of U.S. patent application Ser. No. 14/645,290 filed Mar. 11, 2015, that claims priority to Chinese Pat. App. No. 201410499470.7 filed Sep. 25, 2014. These applications are incorporated by reference, for all purposes.

BACKGROUND OF THE INVENTION

The present invention relates to a mobile communications device and methods of operation. More specifically, embodiments of the present invention relate to a mobile communications device, such as a smart phone, including an ultraviolet light source, and methods of controlling the ultraviolet light source using the smart phone.

The inventor of the present invention is aware of the use of ultraviolet light for disinfectant purposes. Currently, there are few stand-alone products on the market that provide ultraviolet light for cleaning surfaces or purifying water. One such product is a hand held UV wand that is plugged into a wall socket, and waved over surfaces; and another such product is a hand-held unit that runs on batteries, and is inserted to sanitize a bottle of water.

Some drawbacks contemplated by the inventor, to such devices include the high power consumption of such devices limit utility of such devices. For example, surface sanitizers are typically bulky and need to be powered by plugging them into a wall socket; and portable water sanitizers use batteries, but drain them quickly. Additional drawbacks are when the user travels, the user must remember to bring along. Because of gadget overload, such dedicated ultraviolet light (UV) sources are not believed to be widely adopted.

It is desired to have an ultraviolet light source without the drawbacks described above.

BRIEF SUMMARY OF THE INVENTION

The present invention relates to a mobile communications device and methods of operation. More specifically, embodiments of the present invention relate to a mobile communications device, such as a smart phone, including an ultraviolet light source, and methods of controlling the ultraviolet light source using the smart phone.

In some embodiments, a case or dongle for a smart phone is contemplated having an integrated ultraviolet (UV) light source and a power source, e.g. batteries. In such embodiments the UV light source may be located near one or more holes of the case, or anywhere else, where the camera of a smart phone is located. In some embodiments, power for the UV light may be drawn from the smart phone or from the case or dongle.

In some embodiments, a smart phone is contemplated having an integrated UV light located near the camera of a smart phone is located, or anywhere else. In some embodiments, power for the UV light may be drawn from the smart phone.

In some embodiments, application software is installed upon the smart phone, and programs the processor of the smart phone to perform one or more operations. Some operations may include monitoring a camera image or accelerometers, directing the UV light to turn on and off, and the like. In some examples, the camera image may be monitored to determine where the UV light is directed towards, may be monitored to determine whether the UV light is pointed upwards or downwards, etc. In other examples, the camera image may be used to determine if the UV light is close enough to a surface for disinfectant purposes, or the like.

In some embodiments, accelerometers, gyroscopes, etc. may also be used to determine orientation of the smart phone. In particular, if the UV light of the smart phone is directed upwards, the power may be shut-off from the UV light; while the UV light of the smart phone is directed, e.g. within 45 degrees of downwards, the UV light may be turned on, or the like.

In various embodiments, using data from one or more of these sensors, the smart phone may be programmed to indicate to the user how long to hold the UV light source of the smart phone over a particular surface; when a particular surface is sanitized and when to move the UV light source of the smart phone to a new location; or the like. In addition, the smart phone may be programmed to turn off the UV light upon unsafe usage conditions.

According to one aspect of the invention, a device for providing ultraviolet light is disclosed. One device includes a shell for a portable device, wherein the shell includes an interior region and an exterior region, wherein the interior region is adapted to be disposed adjacent to the portable device. An apparatus includes a power source configured to provide electrical power, and an ultraviolet light source coupled to the power source and embedded into the exterior region of the shell, wherein the ultraviolet light source is configured to output the ultraviolet light in response to the electrical power.

According to another aspect of the invention, a method for providing ultraviolet light includes providing a shell having an interior region and an exterior region, wherein the shell comprises an ultraviolet light source embedded into the exterior region of the shell, wherein the ultraviolet light source is configured to output ultraviolet light. A technique may include disposing a portable device adjacent to the interior region within the shell, and powering the ultraviolet light source to cause the ultraviolet light source to output the ultraviolet light to a plurality of surfaces. In other aspects, a method includes coupling a UV source dongle to the portable device, e.g. plugging into an interface/power port of the portable device.

According to one aspect of the invention, a method for a hand-held device is disclosed. One technique includes illuminating, with a first UV LED associated with the hand-held device, a surface of an object with UV light, and acquiring with a visible-light image sensor on the hand-held device, a first image of the surface of the object while the surface of the object is illuminated by the first UV LED. A method includes performing with the processor in the hand-held device, a function upon the first image to determine a type of contaminant disposed upon the surface of the object. In some embodiments, a process may include determining with the processor in the hand-held device, sanitation techniques to perform in response to the type of contaminant that is determined, and displaying with a touch-screen display on the hand-held device, the sanitation techniques to perform to the user. In some embodiments, sanitation techniques may include washing the surface of the object, using a sanitation product on the surface of the object, exposing UV-C light on the surface of the object, and the like.

According to another aspect of the invention, a hand-held device for inspecting a surface of an object is disclosed. One device includes a first light source configured to illuminate the surface of the object, and an image sensor configured to capture with a visible-light image of the surface of the object while the surface of the object is illuminated by the first light source. A system may include a processor coupled to the first light source and the image sensor, wherein the processor is configured to perform a function upon the first image to determine a type of a contaminant disposed upon the surface of the object, wherein the processor is configured to determine sanitation techniques to perform in response to the type of contaminant that is determined, wherein the sanitation techniques includes user instructions, and a touch-screen display coupled to the processor, wherein the touch-screen display is configured to display the user instructions to the user. In some embodiments, the sanitation techniques include UV LED exposure settings, and the touch-screen display is configured to display a UV illumination icon to the user, and the touch-screen display is configured to receive, a user selection of the UV illumination icon. An apparatus may include a second UV-LED coupled to the processor, wherein the second UV-LED is configured to illuminate the contaminant disposed surface of the object with UV light, in response to the UV LED exposure settings, and wherein the processor is configured to receive the user selection of the UV illumination icon and configured to output the UV LED exposure settings to second UV-LED in response thereto. In some embodiments, the first light source may include a visible light source, infrared light source, and/or UV light source.

Additional objects, features and advantages of the present invention can be more fully appreciated with reference to the detailed description and accompanying drawings that follow.

BRIEF DESCRIPTION OF THE DRAWINGS

In order to more fully understand the present invention, reference is made to the accompanying drawings. They are not to be considered limitations in the scope of the invention, the presently described embodiments and the presently understood best mode of the invention are described with additional detail through use of the accompanying drawings in which.

DETAILED DESCRIPTION OF THE INVENTION

Figure 1:
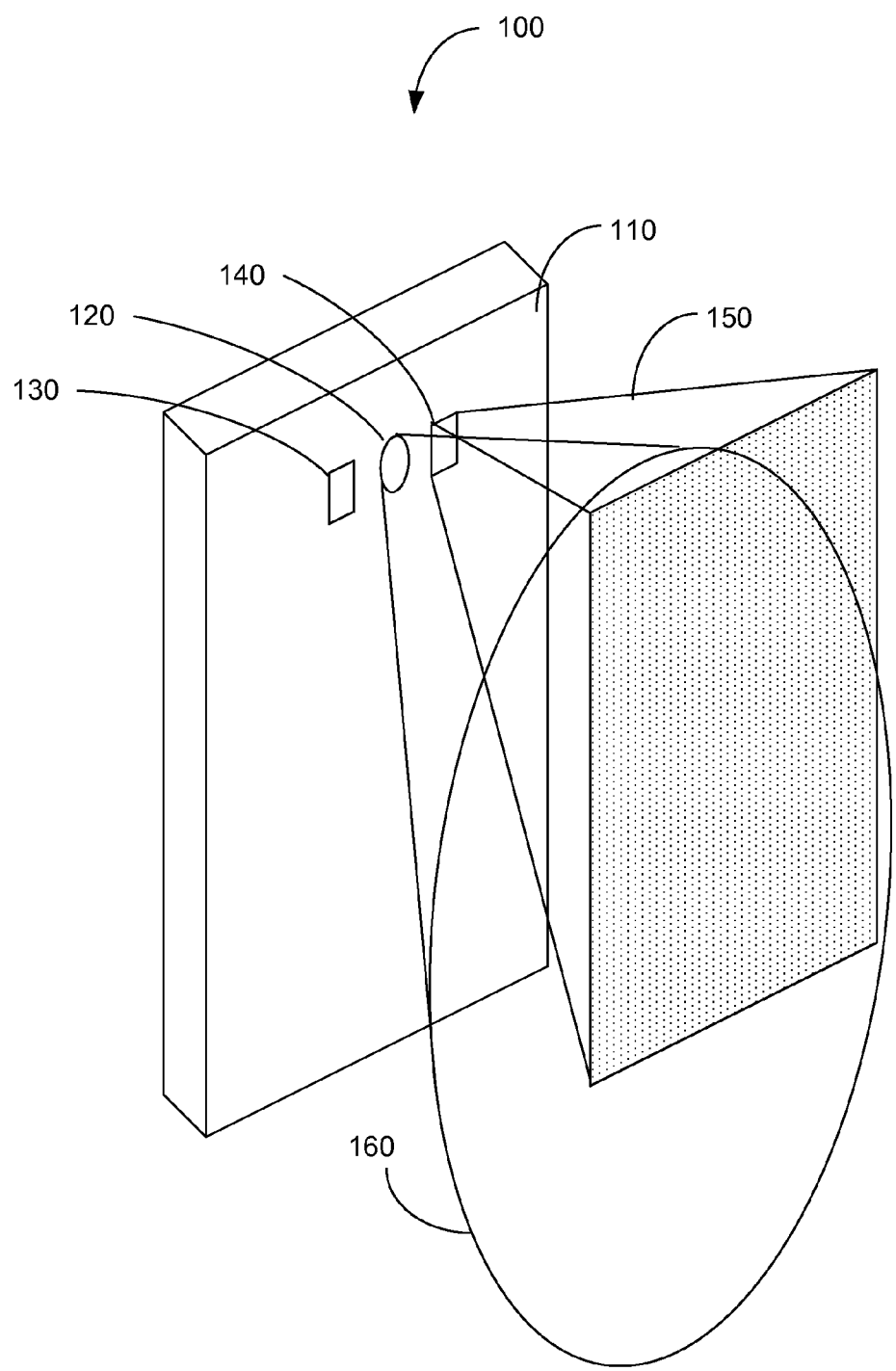
FIG. 1 illustrates an example of various embodiments of the present invention.

FIG. 1 illustrates various embodiments of the present invention. More specifically, FIG. 1 illustrates a hand-held computing device (e.g. smart phone, tablet) 100. In various embodiments, as illustrated, the back casing 110 of device 100, may include a camera 120, a LED light source (e.g. flash) 130, and a UV light source 140. In FIG. 1, UV light source 140 may be positioned such that light 150 from the UV light source 140 is within a field of view 160 of camera 120. In other embodiments, light 150 may not be within field of view 160. UV light source 140 may be positioned on the side, top, bottom, or the like of smart device 100.

Figure 2:
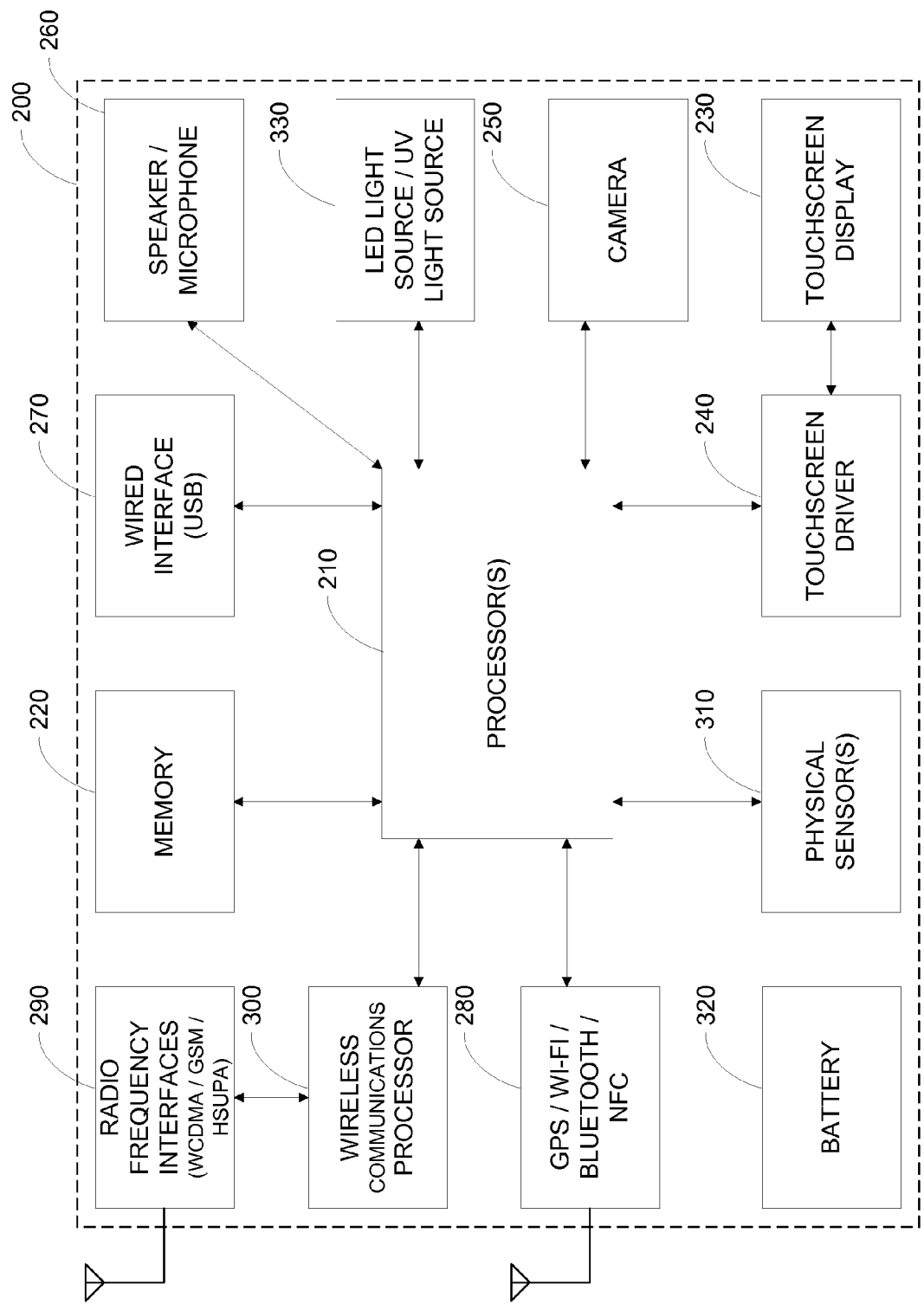
FIG. 2 illustrates a functional block diagram of embodiments of the present invention.

FIG. 2 illustrates a functional block diagram of various embodiments of the present invention (smart device), e.g. iPad, iPhone, Nexus, etc. In FIG. 2, a computing device 200 typically includes an applications processor 210 (e.g. A7 Core, Tegra), memory (including controllers) 220 (e.g. DRAM, Flash), a touch screen display 230 (e.g. OLED, IPS) and driver 240, a camera 250 (e.g. CMOS, CCD), audio input/output devices 260 (speakers/microphone), and the like. Communications from and to computing device are typically provided by via a wired interface 270, a GPS/Wi-Fi/Bluetooth interface 280, RF interfaces 290 (e.g. CDMA, GSM, HSUPA) and processor 300, and the like. Also included in various embodiments are physical sensors 310, e.g. multi-axis Micro-Electro-Mechanical Systems (MEMS) including accelerometers, gyroscopes, magnetometers, pressure sensors, or the like. In various embodiments, operating systems may include iOS, Windows Mobile, Android, or the like.

In some embodiments, computing device may include an integrated UV light source 330. The UV light source 330 may be embodied as a UV light source being developed by the assignee of the present patent application, RayVio, although other sources may also be used. In some embodiments, UV light source 330 may include a UV LED that outputs light within the UV-A range, the UV-B range, and/or the UV-C range.

FIG. 2 is representative of one computing device 200 capable of embodying the present invention. It will be readily apparent to one of ordinary skill in the art that many other hardware and software configurations are suitable for use with the present invention. Embodiments of the present invention may include at least some but need not include all of the functional blocks illustrated in FIG. 2. For example, in some embodiments, the hand-held computing device need not be a multi-purpose smart-device, but may be a dedicated device. Further, it should be understood that multiple functional blocks may be embodied into a single physical package or device, and various functional blocks may be divided and be performed among separate physical packages or devices.

Figure 4A:
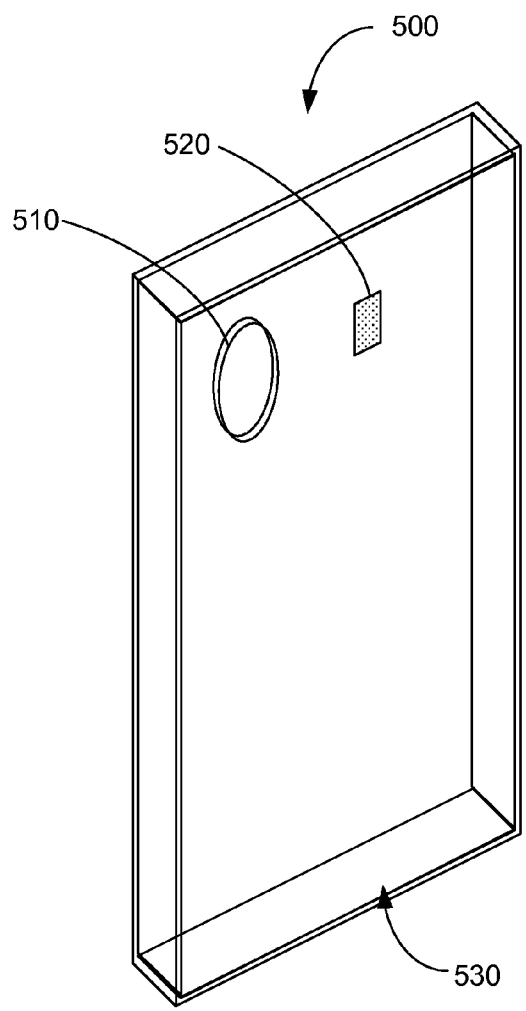
FIGS. 4A-B illustrate examples of various embodiments of the present invention.
Figure 4B:
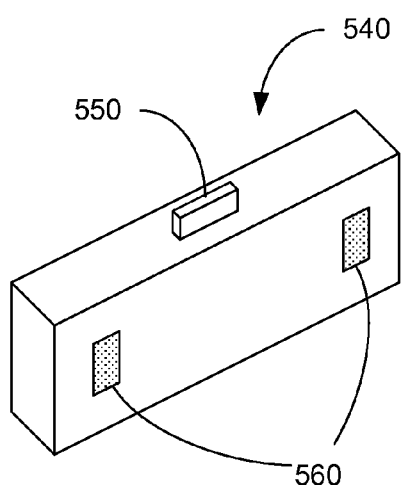

In some embodiments, as illustrated in FIGS. 4A-B, the UV light source may be embodied in a protective case for a smart device (FIG. 4A), and/or a device that can be attached and detached from a smart device (FIG. 4B). As will be discussed below, such devices may include a UV light source, power source, UV controller, physical sensors (MEMS), wired or wireless communications capability, or the like. It should be understood that the processes described herein may be applied to the integrated smart device embodiments discussed in conjunction with FIG. 1, as well as the peripheral embodiments discussed in conjunction with FIGS. 4A and 4B, below.

Figure 3:
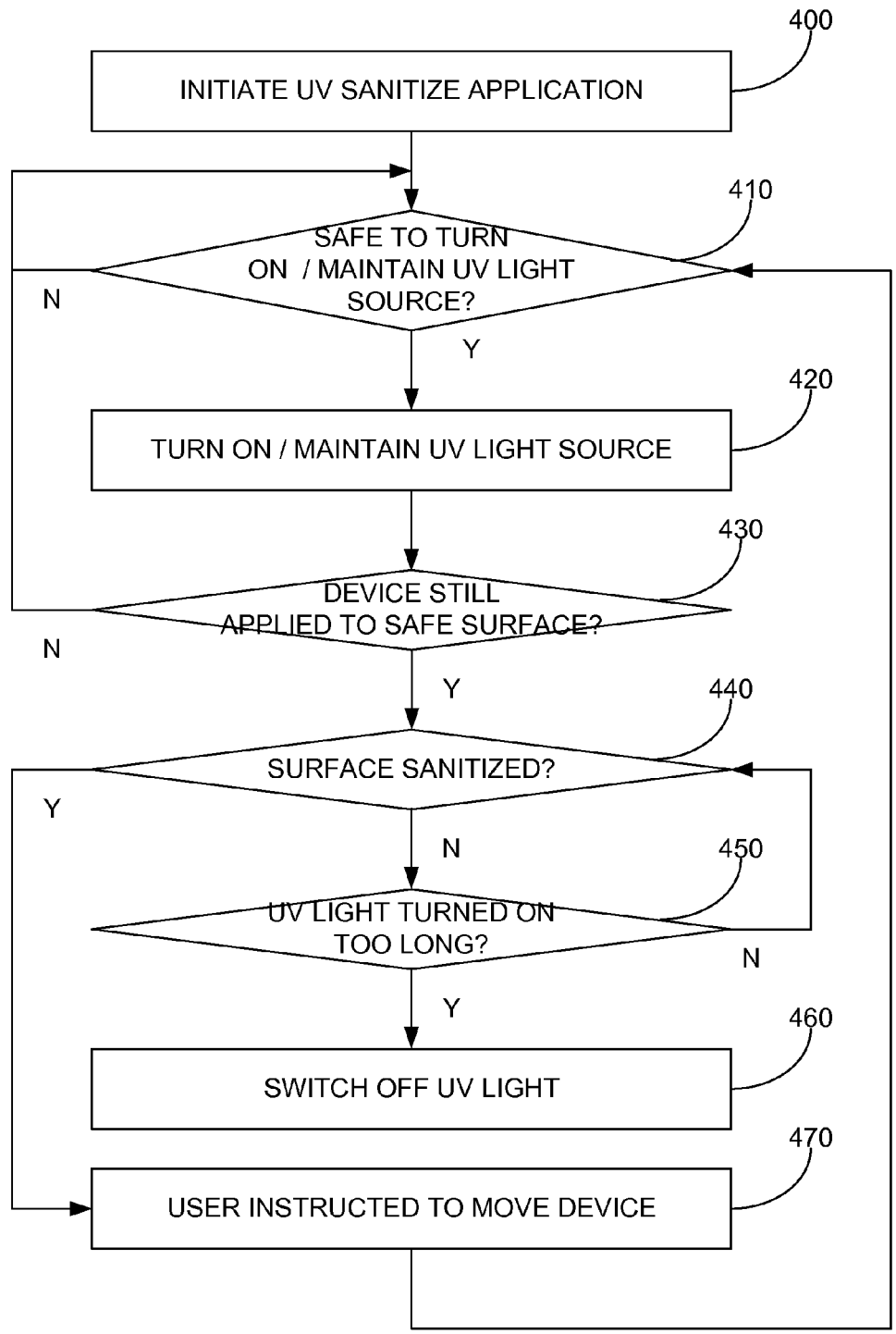
FIG. 3 illustrate block diagrams of flow processes of various embodiments.

FIG. 3 illustrates block diagrams of flow processes according to some embodiments. More specifically, FIG. 3 describes a disinfection or sanitization process. Initially, the user initiates an application (software) upon the smart device to start a UV sanitation process, step 400. This may include the user tapping upon an application icon of a display of the smart device, the user hitting a physical button on the smart device, a software timer going off, or the like.

In some embodiments, the smart device determines whether it is safe to turn on or keep on the UV light, step 410. In some embodiments, this may include the smart device monitoring the MEMS sensors and/or cameras, discussed above, to ensure that the UV light of the smart phone is directed towards a "safe" direction, e.g. the ground, e.g. not upwards towards the face of the user. In some embodiments, this may include the smart device monitoring the amount of light reaching the camera. For example, if there is little light reaching a downwards facing camera, but a lot of light reaching an upwards facing camera, it might be assumed that the UV light faces a surface being sanitized and can be considered safe to be turned on. In another example, if the tilt angle of the downwards orientation is within +/−10 degrees, +/−45 degrees, or the like from downwards, as sensed by the MEMS, the UV light may still be considered safe to be turned on. In some embodiments, based upon the tilt angle, the amount of UV may be varied, for example, at 0 degrees, the UV light may be 100%, at 10 degrees, the UV light may be 50%, etc. In other embodiments, combinations of MEMS sensors and optical detection may be used for this step.

In some embodiments, images from the cameras may be processed by pattern recognition software to provide additional capabilities. The image recognition software may be resident upon the hand-held device and the recognition process may be performed locally on the hand-held device. In other examples, images may be uploaded (via network) to a server and processing may occur on the server. In some examples, images from a downwards facing camera (UV assuming the light is also directed downwards) can be used to help determine if the UV light is directed towards a safe surface for sanitization. In some examples, if the downwards facing camera captures an image of a face, animal, skin, or the like, the UV light may be inhibited; if neither the upwards facing camera nor the downwards facing camera recognizes a face, only then can the UV light may be allowed; or the like. In some embodiments, only groups of specific surfaces can be sanitized, after these surfaces are visually identified. As examples, when surfaces with printed letters, e.g. keyboards, magazines, airplane emergency cards are identified by character recognition software, the UV light source may be enabled. In other examples, surfaces to be sanitized may be enabled and/or identified by bar-code, QR code, image, target, or the other such identifier. In such examples, only surfaces bearing such identifiers can be sanitized. One of ordinary skill in the art will recognize many other examples of image recognition that may be used in various embodiments of the present invention.

In some embodiments, based upon a recognized object, the amount of UV light directed towards the object may be modified. As mentioned above, the recognition process may be performed upon the hand-held (smart) device, or in a remote server. In various embodiments, the hand-held device and/or the remote server may provide an identifier or class of identifier of the object and based upon the identifier, and then the hand-held device modulates the UV power output; and in another embodiment, the server may directly provide the UV power output parameters to the hand-held device, based upon the identified object or class of object, In one example, when an image is recognized to include an orange, the UV exposure time may be 60 seconds, whereas when the image is recognized to include an apple, the UV exposure time may be 20 seconds. The exposure times may be based upon contaminants or pathogens commonly associated with such items, such as *Salmonella* on oranges, *E. Coli* on apples, and the like. In other embodiments, the exposure times may be based upon a type of pathogen/contaminant suspected by the user. In particular, if the user comes upon a rodent nest under their house, they may believe that surfaces and/or insects carry diseases, such as Bubonic plague, or the like. Accordingly, the user may directly select a UV setting. Alternatively, the user may input the suspected type of pathogen, and based upon the pathogen, the UV settings may be provided from the remote server, or stored within the smart device.

In some embodiments, a focus distance of the camera may be used to determine whether the UV light source is inhibited or not. For example, in some embodiments, when camera determines that the surface is within about 6 inches away from the camera/UV light source, the UV light may be activated; and for safety sake, when the distance is further than 6 inches, the UV light source may be deactivated. In various embodiments, the safety measures may be implemented as a combination of hardware and software. In some cases, the user may be able to override safety measure in certain circumstances and turn on the UV light, e.g. with a click-through agreement, age verification, password verification, fingerprint recognition, biometric recognition, or the like. In other cases, certain safety measures may not be overridden, e.g. UV light is turned off if the UV light is pointed upwards and a face is detected in the field of view of the camera.

In some embodiments, the camera flash (e.g. LED) and a photo diode on the hand-held device may also be used to determine the distance of the UV light source from a surface. Such embodiments may rely upon the round-trip time for the light from the camera flash to reflect from a surface and be sensed by the photo diode. In some embodiments, the determined distances (camera focus, round-trip time, proximity detection, etc.) may also be used in determining a power output, duration, duty cycle, or the like for the UV light source. For example, if the determined distance to the surface is 4 inches, the power output of the UV light source may be smaller than if the determined distance to the surface is 36 inches. Alternatively, the power output of the UV light source may be about the same, but the exposure time would be shorter for the surface that is only 4 inches away. In light of the above disclosure, one of ordinary skill in the art will recognize other embodiments may use other combination of the above embodiments.

In various embodiments, if safe, power may be applied to the UV light and one or more timers may be initiated, step 420. When the UV light is turned on, the user may be notified, for example, an auxiliary visible light source may turn on, the display of the smart device may turn blue, a sound may be emitted, a vibration may be produced, etc.

In various embodiments, while the UV light is positioned over a particular surface, the cameras and/or the MEMS sensors may be used to determine whether the smart phone has moved, step 430. In some embodiments, to sanitize a surface, the surface should be exposed to UV light for a certain amount of time. However, if the user moves the UV light around, a keyboard, for example, regions of the keyboard may not be sufficiently exposed to the UV light. Accordingly, based upon optical tracking (from camera images), and/or MEMS sensors, the smart device can recognize what surface the UV light is illuminated.

In various embodiments, based upon pattern recognition and/or image stitching functions, software can determine how long different parts of surface, e.g. a keyboard, have been exposed to UV light. In such an example, the application software can determine that the asdf keys were exposed to UV light for 15 seconds, and thus sanitized, but the jkl; keys were exposed to UV light for only 5 seconds, thus further exposure is necessary. In some embodiments, as the user scans across a surface, multiple images of the surface may be captured and stitched together automatically, and as the UV light is swept across the surface, approximate exposure times for different portions of the surface are associated with portions of the stitched image. In various embodiments, movement sensors may provide feedback regarding an optimal scanning rate of the UV light over the surface.

In some embodiments, the timers may be used to determine whether the UV light has exposed a surface a sufficient period of time, step 440, and/or to determine whether the UV light has been powered on for too long, step 450. In the latter case, the UV light may be automatically switched off, step 460. In other embodiments, many other such timers may be used for similar purposes. The amount of time may vary upon the type of surface to be disinfected, for example, fruit, water, and plastic surfaces may require different exposure times.

In various embodiments, after a particular surface has been exposed to UV light for a sufficient period of time, the smart device may notify the user, e.g. sound, image, vibration. In some embodiments, the user may terminate the above process at any time.

FIG. 4A illustrates another embodiment, a protective housing 500 for a smart device.

As illustrated, protective housing 500 may include an opening 510 where the camera of the smart device is positioned. Additionally, housing may include a UV light source 520, typically near opening 510, and a region 530 for a power source, e.g. battery. In other words, in some embodiments, UV light source 520 receives power from a smart device that is nestled within protective housing 500. For example, a plug, or the like may be provided that physically plugs into a port of the smart device and draws power therefrom. In some embodiments, the port may be an I/O port, power port, peripheral port, USB, Firewire or other ports. In such embodiments, the smart device may control light from UV light source 520 by selectively applying power over the port, as was discussed. In particular, under control of one or more software applications running upon the smart device, the UV light may be turned on or off, and the UV light intensity may be adjusted. In some embodiments, housing 500 communicates with smart device via a wireless communication mechanism, e.g. Bluetooth, NFC, or the like, or a wired connection, e.g. a tether.

In other embodiments, protective housing 500 may include an internal battery, e.g. an external battery pack for the smart device, from which to draw power. In such embodiments, the UV light upon housing 500 may still be under the control of the smart device, as discussed above, and/or under the control of housing 500. For example, housing 500 may have a physical enable button or switch for the UV light, and if enabled, the smart device can power on the UV light source. In another example, housing 500 may have a MEMS device that senses when the UV light is pointed upwards, and disables the UV light from being powered-on, even though the smart phone tries to power-on the UV light. In other embodiments, power may be drawn from the smart device via a USB port, Firewire port, headphone port, or the like.

In various embodiments of housing 500, exposure of UV light source 520 may be within a field of view of a smart device camera. In other embodiments, e.g. relying upon MEMS devices, exposure and field of view for the camera may not overlap. MEMS accelerometers, or the like may be integrated into protective housing 500 in some embodiments, for the purposes previously discussed above.

FIG. 4B illustrates another embodiment of the present invention, a dongle (peripheral) or device 540 for a smart device. In this embodiment, dongle 540 typically includes a physical and/or mechanical interface 550 for attachment onto and detachment from a smart device. In various embodiments, device 540 includes one or more UV light sources 560. Dongle 540 may be self-powered (e.g. via battery) or may be powered by the smart device.

In some embodiments, device 540 may be physically attached to a smart device in operation. The UV light sources 560 may operate with and/or be controlled by smart device, similar to the embodiments described above. Additionally, UV light sources 560 may receive power from smart device or an internal battery.

In other embodiments, device 540 may be physically detached from a smart device in operation. Once detached, the user may point UV light sources 560 towards a surface to sanitize, and active UV light sources 560 through software operating upon the smart device. In some embodiments, device 540 may include a proximity sensor, image sensor, or the like. The sensor may be used by device 540 to determine whether the surface is within a distance, e.g. within 6 inches, of UV light sources 560. If so, device 540 may allow the smart device to activate UV light sources. In some embodiments, device 540 may include position sensors, e.g. MEMS accelerometers, or the like. Such position sensors may also be used by device 540 to determine whether UV light sources 560 are pointed downwards. If so, device 540 may allow the smart device to activate UV light sources.

In some embodiments, device 540 may be relatively water-proof. In some examples, device 540 is separated from the smart device and then immersed in water to disinfect or sanitize the water. As described above, device 540 may be partially controlled by smart device during the sanitization process.

In the various embodiments described above, for sanitization or disinfection purposes, the UV LED light sources are typically within the UV-C band, although UV-A band and UV-B band also provides some degree of sanitization. In such embodiments, a blue-colored LED (and/or a UV-A LED) may also be used. Since UV-C is typically not visible to the human eye, the blue-colored LED is a visual indicator for a user that shows whether the UV-C light is active. Additionally, in some embodiments, the blue LED illuminates the same area as the UV-C LED. Accordingly, the user will sanitize a surface by directing the blue light towards that surface. The supplemental blue LED may be used in any of the above-described embodiments.

Figure 5A:
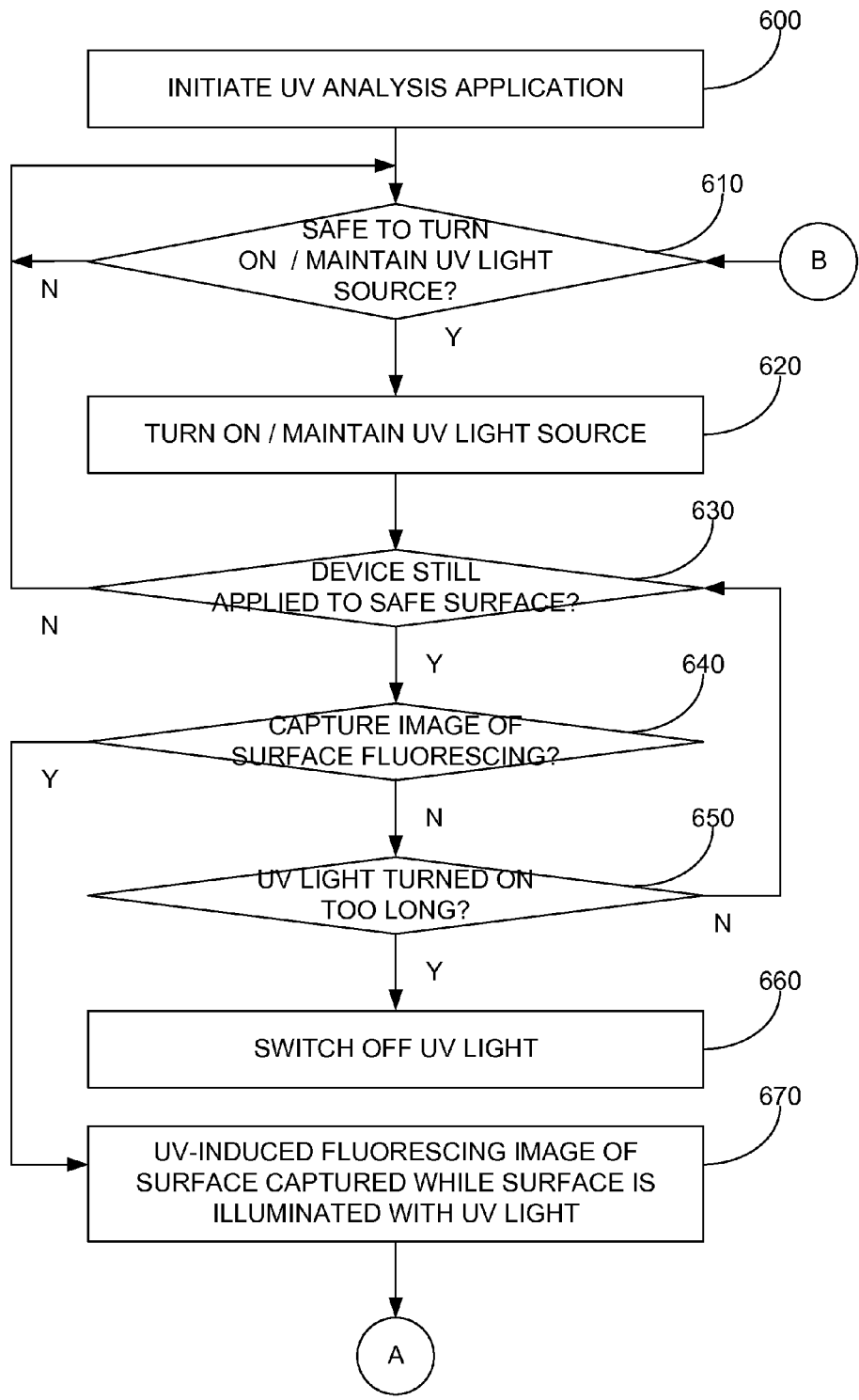
FIGS. 5A-C illustrate block diagrams of flow processes of various embodiments.
Figure 5B:
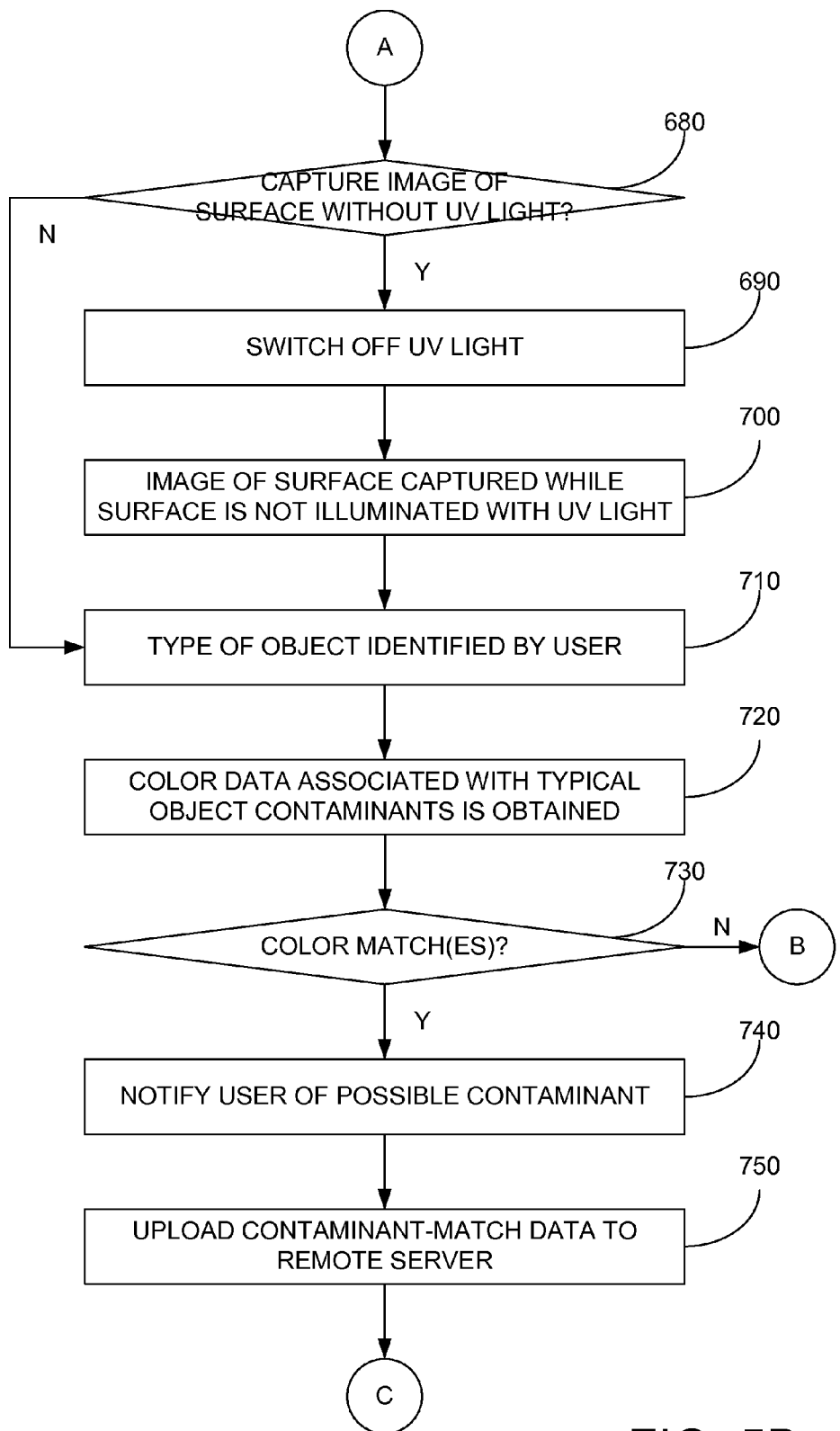
Figure 5C:
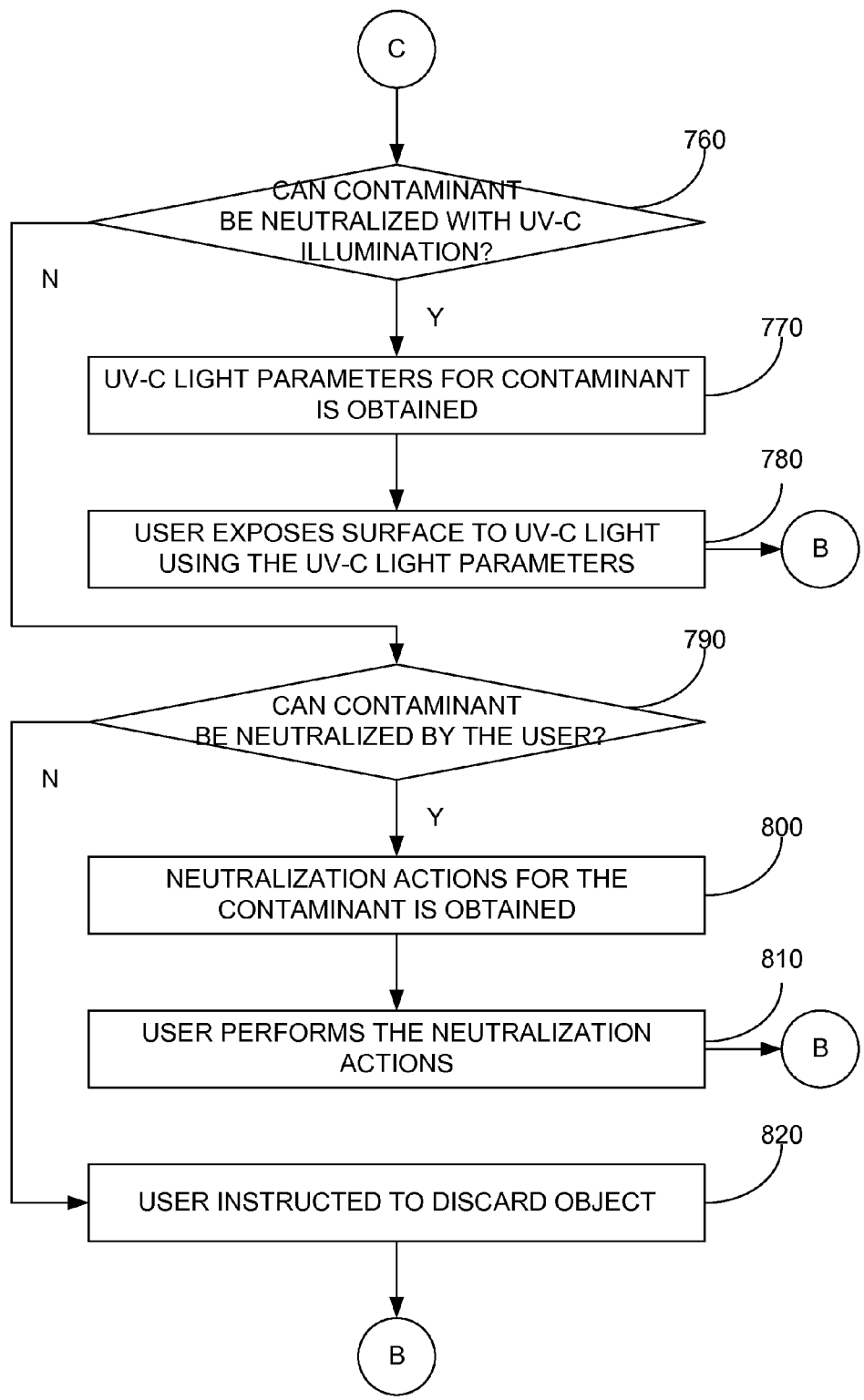

FIGS. 5A-C illustrate block diagrams of flow processes according to some embodiments. More specifically, FIGS. 5A-C describe a UV inspection process. Initially, the user initiates an application (software) upon the smart device to start a UV inspection process, step 600. This may include the user tapping upon an application icon of a display of the smart device, the user hitting a physical button on the smart device, a software timer going off, or the like.

In some embodiments, the smart device determines whether it is safe to turn on or keep on the UV-A light, step 610. Similar to the embodiments described above, the process may include the smart device monitoring the MEMS sensors and/or cameras for unsafe situations. For example, pattern recognition software can be used to ensure the UV-A light is not pointed to a person's face, an animal, or the like; and/or pointed to an appropriate surface, e.g. computer keyboard, printed media, cloth faces, etc. As merely another example, a camera focal distance, a reflected UV light detector, a proximity sensor, or the like may be used to limit the distance between the UV light and the surface.

In various embodiments, if safe, power may be applied to the UV-A wavelength LED and one or more timers may be initiated, step 620. When the UV light is turned on, the user may be notified, for example, an auxiliary visible light source may turn on, the display of the smart device may turn blue, a sound may be emitted, a vibration may be produced, etc.

In various embodiments, in step 630, the safety metrics determined in step 610 are monitored. While still safe, in some embodiments, a software application running on the smart device may allow the user to capture a photograph (e.g. visible spectrum) of the surface, step 640. In some embodiments, no visible-light flash is used when capturing the image, so that the natural fluorescence of the surface in response to the UV-A or UV-C light is captured and stored, step 670. In some examples, driver's licenses, passports, currency, quality or authenticity labels, and the like may include UV-A responsive ink as a fluorescence source. Accordingly, in this step, an image of the fluorescence can be used for bookkeeping, evidentiary purposes, or the like, as described below.

In some embodiments, the image(s) of the UV-induced fluorescence may be due to one or more pathogens, contaminants, residues or the like on a surface of an object. As merely an example, the image may show the fluorescence of bed-bugs on a bed; the image may show the fluorescence of pathogens such as *E-coli, Listeria, Salmonella* and the like on a surface of a fruit or vegetable; the image may show that an egg is contaminated by bacteria or mold; the image may show fecal matter or other biological materials on public bathroom surfaces, medical instruments or food-service or food-preparation regions, or the like.

In some embodiments, the image(s) of the UV-induced fluorescence may be due to the presence of chemicals or the like in an object. As merely an example, the image of a water sample may show presence of chemical contaminants, and the like; the image of a leaf may show the fluorescence of pesticides, fertilizers, or other chemicals on the surface of a leaf, or the like.

In some embodiments, the fluorescence may be due to a change of natural chemicals or change of composition that is detectable on the surface of an object. As merely an example, the image of a fresh egg may be pink in color (due to ooporpherin pigment on a fresh egg), whereas the image of an older egg may be more violet; the image of a surface of an item can indicate the age, composition, origin, quality, of a food or beverage item, such as cheese, milk, meat products, edible oils, wheat, rice, alcoholic beverages, sugars, fruit and vegetables, and the like.

In some embodiments, a visible-light flash may be used during image capture. For example, it is contemplated that the UV-A light source may be used by a user to physically inspect a surface, e.g. passport, for authentication purposes. Subsequently, when the user wants to take a picture of the surface without UV illumination, step 680, the UV light source is turned-off, step 690, and an image of the surface is captured and stored, step 700. In some embodiments, the flash is activated so a visible light image of the surface may be captured. Again, the visible light image may be used for bookkeeping, evidentiary purposes, or the like. As merely an example, the image may be a driver's license of a person going through airport security.

In various embodiments, contaminant detection and/or contaminant handling are then performed. In one embodiment, a user may indicate what type of object is being inspected, and or what type of object is captured in the steps above, step 710. In various examples, one or more hierarchical graphical user interfaces may be output to the user to enable the selection of the type of object. For example, a top GUI may include the general categories: fruit, vegetable, liquid, dairy, clothing, hard surfaces, and the like; and respective secondary GUIs may include pictures of bananas, apples, oranges, grapes, etc.; carrots, lettuce leaves, onions, broccoli, etc.; water, etc.; milk, eggs, cheese, etc.; silk, wool, spandex, cotton, etc.; diaper changing surfaces, toilet seats, chopping boards, etc. In other embodiments, the user may select the object name from a textual list, or the like.

In response to the user identification of the object, data associated with the object may be obtained from memory, step 720. The data may include colors of typical contaminants (including pathogens, chemicals, other characteristics of the object that may be captured, or the like) as they fluoresce under UV light. As an example, for fresh eggs, under UV light, the surface will appear pink-ish, whereas for older eggs, the surface will appear violet or black. In other embodiments, the contaminants (including pathogens, and the like, described above) may be retained in memory and used for all or more than one object. In other words, the types of impurities upon the surface of the objects may be detected for all or multiple objects. As an example, for all fruits and vegetables, the data obtained in this step may include characteristic colors of common bacteria such as *E-coli, salmonella, listeria*; pesticide residue; fecal residue; and the like.

In some embodiments, the fluoresced-color data associated with contaminants, and the like may be stored locally, within a disinfection/identification application, and/or the color data may be retrieved from a remote server. The latter embodiments may be helpful in times of mass sickness outbreaks, such as SARS, MERS, Ebola, or the like. In such cases, as users become concerned with picking up such diseases, their smart devices may automatically receive (and or query for) the fluoresced-color data associated with such diseases. For example, when an outbreak becomes public, a traveler can quickly receive UV-induced color data associated with the outbreak from a server, and the traveler can inspect his hands, clothing, a room, an airline seat, and the like for the pathogen.

In various embodiments, the colors in the UV-induced fluorescent image acquired in step 670 are compared to the color data of the contaminants obtained above (step 720), step 730. If there is no match, the process may return to step 610, and the user may continue to scan other objects/surfaces for contaminants.

If the colors substantially match, the user is notified of the possible contaminant (including pathogen, chemical, etc.), step 740. In various embodiments, the notification may include the hand-held device vibrating, producing a sound, displaying a warning on the display, and the like. Accordingly, the user is made aware of possibly contaminated food before the user consumes it or purchases it.

In additional embodiments, if there is a match, the indication of the match, the object type, the geographical coordinates of the match, and the like may be uploaded to a remote server, step 750. By aggregating such data in a remote server, "hot spots" of contaminants, can be identified in real-time. Accordingly, locations of outbreaks of diseases, for example, can be quickly located, isolated, and/or decontaminated. In other examples, such data can help identify sources of chemical pollution by identifying and studying how the pollutants are being geographically dispersed, before people are harmed by such pollution. In still other examples, such data can help identify sources of contaminated food by identifying where the contaminated food is found and studying suppliers of such food. The benefits to such actions include identification of sources of contaminated food possibly before a mass outbreak of sickness actually occurs.

In various embodiments, a determination is made as to whether the user can attempt to de-contaminate the surface with UV light, step 760. In certain configurations of a hand-held device, described above, a UV-LED light source providing light within the UV-C band (UV-C light source) is provided. In this step, a determination is made as to whether exposure of the UV-C light can destroy the contaminant. For example, for pathogens such as *E-coli, Salmonella*, and *Listeria*, application of UV-C light can destroy them; whereas for chemical pollution, such as fertilizers and insecticides, UV-light cannot neutralize them. In cases where UV-C light is used, the processor in the hand-held device may retrieve parameters (e.g. exposure times, exposure power, etc.) from local memory, or from a remote-server, step 770.

In certain embodiments, when such parameters are obtained in real-time from the remote server, the remote server may provide different UV-C light parameters for different geographical regions, for different intensities of detection, and the like. Such embodiments may be useful for running UV treatment experiments upon the contaminants. For example, in region A, if a contaminant is detected, a UV treatment time is short, but the UV intensity is high; in region B, a UV treatment time is long, but the UV intensity is low; in region C, a UV treatment time is short and the UV intensity is short; and the like. As will be described below, the contaminant inspection process may be repeated by the user, until the object is safe to eat, accordingly, the experiments describe above are fully ethical. Such experiments can help determine more optimal and effective UV treatment parameters for the identified contaminants, and these optimal UV treatment parameters can then be widely distributed. In other cases, if the contaminants show widely different effective UV treatment parameters, this may help identify locations of weaker strains of the contaminants and locations of stronger strains of the contaminants. The identification of different strains may help scientist use the weaker strains to combat the stronger strains, and the like.

In various embodiments, after receiving the UV-C light parameters, the user is given instructions on how to point the UV-C light source at the contaminated area, and expose the surface to the UV-C light, step 790. Various steps in the process described above may then be repeated by the user to determine whether the UV-C treatment is successful.

In embodiments where the contaminants are not treated with UV-C light, a determination is made whether the user can take other actions to make the surface clean, step 790. For example, for pathogens such as *E-coli, Salmonella*, and *Listeria*, and chemical pollution, such as fertilizers and insecticides, a through washing of the surface of the object may remove such contaminants. For consumable objects, washing with clean hot water may be sufficient; whereas for food preparation surfaces, washing with a dilute bleach solution may be required. In various embodiments, the types of ameliorative actions may be stored and retrieved from a memory within the hand-held device, or received from a remote-server, step 800.

In certain embodiments, when the actions are obtained in real-time from the remote server, the remote server may also provide different actions for different geographical regions, for different intensities of detection, and the like. Such embodiments may be useful for running cleaning experiments upon the contaminants, such as, in region A, a bleach solution is used; in region B, hot water is used; in region C, dish washing soap is used; and the like. As the contaminant inspection process is repeated by the user, until the object is safe to eat, such experiments are ethical and can help determine more optimal and effective treatment methods. In other cases, if the contaminants show widely different responses to cleaning, this may again help identify locations of weaker strains of the contaminants and locations of stronger strains of the contaminants.

In various embodiments, after the user is given the cleaning instructions, the user performs the actions, step 810. Various steps in the process described above may then be repeated by the user to determine whether the cleaning is successful.

In various embodiments, if the contaminant cannot be neutralized by UV or surface cleaning, the user is instructed to discard the object or select a different object to buy, step 820. The process above may then be repeated.

Returning to FIG. 5A, in various embodiments, a determination is made whether the UV light has been powered on for too long, step 650. In the latter case, the UV light may be automatically switched off, step 660. In other embodiments, many other such timers may be used for similar purposes. The amount of time may vary upon the intensity of the UV light, the temperature, and the like.

Further embodiments can be envisioned to one of ordinary skill in the art after reading this disclosure. For example, in some embodiments, a UV light sensor may be included on the smart device, protective case, dongle, or the like. The UV light sensor may be positioned proximate to the one or more UV light sources. In operation, the UV sensor may be used to determine if UV light is reflected from a surface, and/or an intensity of reflected UV light. In one embodiment, when reflected UV light is not detected, the UV light source may not be pointed at a surface, for example, the UV light source may be pointed into space. In such an embodiment, the amount of UV light output from the UV light sources may be decreased or pulsed for safety's sake. When reflected UV light is subsequently detected by a UV light sensor, it may be assumed that UV light is reflecting off of a relatively close surface. Accordingly, the UV light source output may be increased to the desired UV light intensity. In some embodiments, if too much reflected UV light is detected, the UV light intensity may be decreased.

Some of the above examples are directed to food or liquids contaminants that may harm a human or animal, but are not limited to food. In particular, embodiments may be directed to goods and the detection of counterfeit goods. For example, a user can identify a good and perform a UV scan on a portion of the good, e.g. quality tag, and capture images of the good fluorescing. The image can then be compared to authentic images to help the user determine the authenticity of a good. Additionally, if a counterfeit object is detected, the indication may be sent to a remote server for further action. For example, the remote server may be associated with a manufacturer, a governmental agency, or the like.

In other embodiments, combinations or sub-combinations of the above disclosed invention can be advantageously made. For example, in some embodiments, the UV light peripheral may be stored separate from the smart device. In operation, the user would plug-in the UV peripheral into the smart device, and the UV peripheral would draw power and/or receive instructions from the smart device. Software applications running on the smart device would then selectively activate and deactivate the UV light source on the UV peripheral. When disinfecting, the user would then move their smart device (and the attached UV light source) over the treatment surface. After satisfactory completion, the user may detach the UV light peripheral from the smart device, and physically store the peripheral separate from the smart device. In other embodiments, the UV light peripheral may be stored adjacent to the smart device. The block diagrams of the architecture and flow charts are grouped for ease of understanding. However, it should be understood that combinations of blocks, additions of new blocks, re-arrangement of blocks, and the like are contemplated in alternative embodiments of the present invention.

UV light may be used for other purposes than disinfecting or sanitizing a target surface. For example, in some embodiments, UV light from the above-described UV light sources may also be used for detection of contaminants upon a target surface. In some embodiments, UV light (including light in the UV-A, UV-B, and UV-C wavelength range) may be output by one or more UV light sources, in response, certain contaminants (e.g. bacteria, virus, insects, bodily fluids, etc.) upon target surface will fluoresce. In one embodiment, the fluorescence of the contaminants may then be directly seen by a user, and the user will know that the surface is dirty, unsafe, or the like. Accordingly, in some embodiments, no UV sanitation step is required.

In various embodiments, with continuous or high power to the UV light sources (for detection and/or sanitation, the inventors are concerned about the safety of the device to users. As was discussed above, a number of safety mechanisms, including use of an accelerometer, tilt sensor, image recognition programs, and the like, can be incorporated into various embodiments to increase user safety In various embodiments, additional techniques for increasing user safety are contemplated. As merely an example, in some embodiments, non-continuous or low UV illumination of a UV light source may be used for contaminant detection. In some embodiments, a first picture of a surface is taken under natural light, camera flash, or the like; the UV light source is quickly turned on or pulsed and while the contaminants are fluorescing a second picture of the surface is taken; and the UV light is turned off. In other embodiments, the order of taking pictures may be reversed. Next, using appropriate image processing techniques, such as image normalization, equalization, subtraction, and the like, an image is generated representing the contaminants. This image can then be displayed to the user on the display of the hand-held computing device (e.g. smart phone). Additionally, the image may be uploaded to a remote server. In some embodiments, the processed images along with GPS coordinates may be saved upon the hand-held device and/or sent to the remote server. The process above may be repeated for different surfaces or the same surface in response to the user clicking a hardware or software button on the hand-held computing device, dongle, or the like. In various embodiments, these image detection steps may be a part of the image recognition process described above, and based upon the recognized objects, the appropriate UV treatment process may then be performed.

Advantages to these detection embodiments include that the contaminant state of a hotel room, a restaurant table and utensils, a bathroom, an airplane seat-back, or the like can be documented by the user and/or the remote server (e.g. Yelp!, Tripadvisor, a security or safety-oriented server or website, etc.). Additionally, if combined with the sanitation/treatment embodiments, described above, the user can document the "before" and "after" state of contaminants on a target surface. Other advantages to the above embodiments include that since the output of the UV light source is a short burst for detection, as opposed to a continuous or high output of the UV light source for sanitation, the potential for UV light to adversely harm a user is greatly reduced. More particularly, in one embodiment, the detection process may only utilize a short 10 ms burst of UV light at lower than about 100-200 milliwatts.

In some embodiments of the present invention, the inventors are aware that most image sensors on hand-held devices (e.g. phones, tablets, cameras) are based upon ranges of red, green, and blue colored filters. Accordingly, detection of the color of UV-induced fluorescent may be approximate. In various embodiments, to increase the color-matching accuracy a prismatic structure, grating structure, and the like may be interposed between the surface of the object and the camera. In various embodiments, the prismatic structure may be removably disposed upon the lens of the camera when using the process described therein. In operation, the colors of the fluorescence are spread across the image sensor, such that spatial position is associated with spectral frequency. As an example, suppose a first contaminant is associated with a red fluorescent peak at 700 nm, and a second contaminant is associated with red fluorescent peaks at 680 and 720 nm. In such a case, if UV-induced fluorescent light is spread spatially, using a grating, and shows two peaks at about 680 nm and 720 nm, it is likely that the contaminant is the second contaminant. In some embodiments, other types of light sources may be used to cause a surface to fluoresce instead of UV-A, UV-B, or UV-C, such as visible light, black-light, infrared, and the like. In light of the present disclosure, it is believed that one of ordinary skill in the art will recognize other configurations and operations that are within the scope of embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A method for a hand-held device comprising:
    illuminating, with one or more UV LEDs associated with the hand-held device, a plurality of surfaces other than a surface of the hand-held device, wherein the plurality of surfaces includes a surface of an object with UV light;
    acquiring with a visible-light image sensor on the hand-held device, a first image of the surface of the object while the surface of the object is illuminated by the one or more UV LEDs;
    performing with the processor in the hand-held device, a function upon the first image to determine a type of contaminant disposed upon the surface of the object;
    determining with the processor in the hand-held device, sanitation techniques to perform in response to the type of contaminant that is determined, wherein the sanitation techniques includes UV LED exposure settings and user instructions;
    displaying with a touch-screen display on the hand-held device, the user instructions to the user and a UV illumination icon;
    receiving with the touch-screen display on the hand-held device, a user selection of the UV illumination icon; and
    illuminating, with the one or more UV LEDs associated with the hand-held device, the surface of the object with UV light to modify the contaminant disposed upon the surface of the object, in response to the UV light exposure settings and the user selection of the UV illumination icon.

2. The method of claim 1
wherein a UV LED the one or more UV LEDs consists of a single UV LED; and
wherein the single UV LED emits UV light within the UV-C band.

3. The method of claim 1
wherein the one or more UV LEDs comprises a first UV LED and a second UV LED;
wherein the first UV LED illuminates the surface of the object with UV light within the UV-A band; and
wherein the second UV LED illuminates the surface of the object with UV light within the UV-C band.

4. The method of claim 1 wherein the user instructions comprise: instructions to wash the object, and instructions on how to move the hand-held device over the surface of the object.

5. The method of claim 1 wherein the UV LED exposure settings comprises intensity settings, duration, and distance settings.

6. The method of claim 5 further comprising:
determining an actual distance between the hand-held device and the surface of the object;
determining adjusted intensity settings and/or an adjusted duration in response to the actual distance; and
wherein the illuminating, with the one or more UV LEDs associated with the hand-held device, the surface of the object comprises illuminating, with the one or more UV LEDs associated with the hand-held device, the surface of the object with UV light in response to the adjusted intensity settings and/or the adjusted duration, and the user selection of the UV illumination icon.

7. The method of claim 1 a visible-light image of the surface of the object comprises two-dimensional spatial spectral information.

8. The method of claim 1 further comprising:
receiving a selection with the touch-screen display of the hand-held device, a user indication of an object type of the object; and
wherein the performing with the processor in the hand-held device, the function upon the first image comprises performing with the processor in the hand-held device, the function upon the first image to determine the type of contaminant disposed upon the surface of the object, in response to the object type.

9. The method of claim 8 wherein the function comprises matching a color of the first image to a table of colors associated with a plurality of contaminants associated with the object type to determine the type of contaminant disposed upon the surface of the object.

10. The method of claim 1 further comprising:
sending with the processor in the hand-held device, an indication of the type of contaminant, and geographic coordinates of the hand-held device, to a remote server; and
receiving the sanitation techniques to perform from the remote server.

11. The device of claim 1
wherein the touch-screen display is configured to receive a selection of an object type of the object; and
wherein the processor is configured to perform the function upon the first image to determine the type of contaminant disposed upon the surface of the object, in response to the object type.

12. The device of claim 11 wherein the function comprises matching a color in the visible-light image to a table of colors associated with a plurality of contaminants associated with the object type to determine the type of contaminant disposed upon the surface of the object.

13. A hand-held device for inspecting a surface of an object not associated with the hand-held device comprising:
a one or more UV LEDs configured to illuminate a plurality of surfaces other than surfaces of the hand-held device, wherein the plurality of surfaces includes the surface of the object;
an image sensor configured to capture with a visible-light image of the surface of the object while the surface of the object is illuminated by the one or more UV LEDs;
a processor coupled to the one or more UV LEDs and the image sensor, wherein the processor is configured to perform a function upon the first image to determine a type of a contaminant disposed upon the surface of the object, wherein the processor is configured to determine sanitation techniques to perform in response to the type of contaminant that is determined, wherein the sanitation techniques includes UV LED exposure settings and user instructions;
a touch-screen display coupled to the processor, wherein the touch-screen display is configured to display the user instructions and a UV illumination icon to the user, wherein the touch-screen display is configured to receive, a user selection of the UV illumination icon;
wherein the one or more UV LEDs is configured to illuminate the contaminant disposed surface of the object to with UV light, in response to the UV LED exposure settings; and
wherein the processor is configured to receive the user selection of the UV illumination icon and configured to output the UV LED exposure settings to the one or more UV LEDs in response thereto; and
wherein the hand-held device is configured to be physically moved over the plurality of surfaces by the user to provide the UV light to the plurality of surfaces other than the surface of the hand-held device.

14. The device of claim 13
wherein the one or more UV LEDs comprises a single UV LED; and
wherein the single UV LED emits UV light within the UV-C band.

15. The device of claim 13
wherein the one or more UV LEDs comprises a first UV LED and a second UV LED;
wherein the first UV LED illuminates the surface of the object with UV light within the UV-A band; and
wherein the second UV LED illuminates the surface of the object with UV light within the UV-C band.

16. The device of claim 13 wherein the user instructions comprise: instructions to wash the object, and instructions on how to move the hand-held device over the surface of the object.

17. The device of claim 13 wherein the UV LED exposure settings comprises intensity settings, duration, and distance settings.

18. The device of claim 17
wherein the image sensor comprises a focus detection portion configured to determine an actual distance between the image sensor of the hand-held device and the surface of the object;
wherein the processor is configured to determine adjusted intensity settings and/or an adjusted duration in response to the actual distance; and wherein the one or more UV LEDs is configured to illuminate the contaminant disposed surface of the object to with UV light, in response to the adjusted intensity settings and/or the adjusted duration, and the user selection of the UV illumination icon.

19. The device of claim 13 further comprising:
a grating disposed between the image sensor and the object; and
wherein the visible-light image of the surface of the object comprises two-dimensional spatial spectral information.

20. The device of claim 13 further comprising:
a geographic positioning portion coupled to the processor, wherein the geographic positioning portion is configured to determine a geographic position of the hand-held device; and
a communications portion coupled to the processor, wherein the communications portion is configured to send an indication of the type of contaminant, and the geographic position to a remote server.

* * * * *